(12) United States Patent
Motlagh et al.

(10) Patent No.: US 11,833,008 B1
(45) Date of Patent: *Dec. 5, 2023

(54) DENTAL APPLIANCE AND METHOD FOR ADJUSTING AND HOLDING THE POSITION OF A USER'S JAW TO A RELAXED POSITION OF THE JAW

(71) Applicant: Myohealth Technologies LLC, Portland, OR (US)

(72) Inventors: Maryam M. Motlagh, Portland, OR (US); Martin E. Burbano, Portland, OR (US)

(73) Assignee: Myohealth Technologies, Inc., Portland, OR (US)

( * ) Notice: Subject to any disclaimer, the term of this patent is extended or adjusted under 35 U.S.C. 154(b) by 271 days.

This patent is subject to a terminal disclaimer.

(21) Appl. No.: 17/164,698

(22) Filed: Feb. 1, 2021

Related U.S. Application Data

(63) Continuation of application No. 15/724,089, filed on Oct. 3, 2017, now Pat. No. 10,945,818.

(60) Provisional application No. 62/403,327, filed on Oct. 3, 2016.

(51) Int. Cl.
*A61C 7/36* (2006.01)
*A61C 19/05* (2006.01)
*A61F 5/56* (2006.01)
*A61C 7/08* (2006.01)

(52) U.S. Cl.
CPC ............ *A61C 7/36* (2013.01); *A61C 7/08* (2013.01); *A61C 19/05* (2013.01); *A61F 5/566* (2013.01); *A61F 2005/563* (2013.01)

(58) Field of Classification Search
CPC .. A61C 7/08; A61C 7/36; A61C 19/05; A61F 5/566; A63B 71/085
See application file for complete search history.

(56) References Cited

U.S. PATENT DOCUMENTS

| | | | |
|---|---|---|---|
| 4,063,552 A | 12/1977 | Going et al. |
| 4,337,765 A | 7/1982 | Zimmerman |
| 4,362,509 A | 12/1982 | Sule |
| 4,571,186 A | 2/1986 | Pipko |
| 4,573,919 A | 3/1986 | Sinkora |

(Continued)

FOREIGN PATENT DOCUMENTS

CA 2623055 4/2007

OTHER PUBLICATIONS

Prior art: Image of intracoronal attachments (connector & retainer), 1 page.

(Continued)

*Primary Examiner* — Jacqueline T Johanas
*Assistant Examiner* — Shannel Nicole Belk
(74) *Attorney, Agent, or Firm* — Klarquist Sparkman, LLP

(57) ABSTRACT

The disclosed dental appliance is a functional daytime and nighttime anatomical removable dental appliance that is designed to overlay the existing natural dentition of the user. In desirable embodiments, the appliance can be held in place without any alterations to the user's existing dentition. The appliance is a plural piece or plural section intra-oral removable appliance with occlusal surface portions that have been built up to occupy the measured intra-occlusal spaces that exist between pairs of upper and lower teeth when the mandible is in a relaxed or rest position.

19 Claims, 8 Drawing Sheets

(56) References Cited

U.S. PATENT DOCUMENTS

| | | | |
|---|---|---|---|
| 4,661,068 A | 4/1987 | Harrison et al. | |
| 5,562,106 A | 10/1996 | Hecke et al. | |
| 5,879,155 A * | 3/1999 | Kittelsen | A63B 71/085 |
| | | | 128/861 |
| 6,082,363 A | 7/2000 | Washburn | |
| 6,178,967 B1 * | 1/2001 | Barnes, Sr. | A63B 71/085 |
| | | | 128/859 |
| 7,357,637 B2 | 4/2008 | Liechtung | |
| 7,844,340 B2 | 11/2010 | Pawlowicz, III | |
| 8,449,296 B2 | 5/2013 | Liechtung | |
| 8,667,971 B2 | 3/2014 | Makkar et al. | |
| 8,689,795 B2 | 4/2014 | Lee et al. | |
| 10,945,818 B1 * | 3/2021 | Motlagh | A61C 7/08 |
| 2004/0154626 A1 | 8/2004 | Washburn et al. | |
| 2005/0022824 A1 | 2/2005 | Ball | |
| 2009/0061375 A1 | 3/2009 | Yamamoto et al. | |
| 2010/0104998 A1 * | 4/2010 | Farrell | A61C 7/36 |
| | | | 128/861 |
| 2010/0288290 A1 | 11/2010 | Lee et al. | |
| 2011/0185525 A1 | 8/2011 | Stapelbroek et al. | |
| 2013/0040266 A1 | 2/2013 | Kline | |
| 2014/0109919 A1 * | 4/2014 | Crout | A61F 5/56 |
| | | | 128/861 |
| 2014/0174455 A1 * | 6/2014 | Gorman | A61F 5/566 |
| | | | 128/848 |
| 2014/0238418 A1 | 8/2014 | Turkbas | |
| 2016/0128803 A1 | 5/2016 | Webber et al. | |
| 2018/0014962 A1 | 1/2018 | Lee et al. | |
| 2018/0021110 A1 | 1/2018 | Nesbit et al. | |
| 2018/0056167 A1 | 3/2018 | Wisniewski | |
| 2018/0185188 A1 | 7/2018 | Lambert | |
| 2019/0053877 A1 | 2/2019 | Hung | |
| 2020/0037951 A1 * | 2/2020 | Haggiag | A61C 9/00 |

OTHER PUBLICATIONS

Prior art: Image of partial dentures; 1 page.
Prior art: Image of The Precision Attachment Case, 1 page.

* cited by examiner

DENTAL APPLIANCE AND METHOD FOR ADJUSTING AND HOLDING THE POSITION OF A USER'S JAW TO A RELAXED POSITION OF THE JAW

CROSS REFERENCE TO RELATED APPLICATION

This application is a continuation of U.S. patent application Ser. No. 15/724,089, filed Oct. 3, 2017, which claims the benefit of U.S. Provisional Application No. 62/403,327, filed Oct. 3, 2016, which applications are incorporated by reference herein.

FIELD

This disclosure relates to dental appliances for wearing by individual patients or users.

BACKGROUND

A common problem with single piece removable occlusal appliances that cover the entire dental arch, is that they undergo a significant amount of torque across the dental arch when installed which may lead to fracture of the appliance. Often times, such appliances are non-functional and are made too bulky to avoid fracture, negatively impacting the tongue space, phonetics and mastication. A need exists for an improved sectional and functional dental appliance which takes up less intra oral volume, allows the user to speak and masticate with, yet be designed where it is less inclined to fracture.

SUMMARY

The disclosed dental appliance is an anatomical removable sectional dental appliance, such as of a tooth colored resin material, which is designed to temporarily change the occlusion of the user by overlaying the existing dentition of the user, such as from the facial gingival line, across the occlusal table and to the lingual gingival line or lingual height of contour. Sometimes, malocclusion only involves a single section of the dental arch as opposed to the entire dental arch; in which case only a single section or portion of the appliance would be used (e.g., one posterior section or portion or one anterior section or portion would be used). At other times, the malocclusion involves two sections of a dental arch (such as two posterior sections or an anterior section and one posterior section of the dental arch); in which case two dental appliance sections or portions would be used. Often, malocclusions involve all three sections of a dental arch (an anterior section and posterior sections at both sides of the user's mouth); in which case two posterior and one anterior appliance sections or portions would be used. The occlusal portions of the dental appliance portions are built up to temporarily alter the biting surface of the teeth in an attempt to support the user's resting mandibular position during chewing and function. The term removable includes the temporary adherence of the appliance to the existing dentition with temporary dental adhesives, such as applied by either the user or a dentist. In desirable embodiments, the appliance can be held in place without any alterations to the user's existing dentition.

The appliance can therefore be used as an individual appliance section covering only the anterior or one of unilateral posterior sections of the dental arch, or it can be used as a combination of several sections covering the entire dental arch if needed as a plural piece or section intra-oral removable appliance. The sections in a plural section appliance are desirably comprised of an anterior section and at least one posterior section covering the posterior dentition at one side of the user's mouth or two posterior sections, each covering a respective side of the posterior dentition of the user. The appliance sections each desirably have the unique feature of being functional, meaning that it can be worn during chewing and also continuous periods of time, including daytime and nighttime, twenty four hour periods for several months or longer depending on the treatment objective. The appliance is designed to occupy a measured space between occlusal surfaces of user's opposed teeth to improve the occlusion of the teeth in that section of dentition covered by the appliance in an attempt to support the jaw in a comfortable position at times when worn, even during mastication.

The posterior or lateral sections and the anterior section of the appliance are independent sections and can be disconnected separate appliance portions when worn by a user. Alternatively, the mesial and distal end portions of the independent appliance portions can be detachably interconnected when worn. Thus, the end portions (distal end portions) of the anterior section or appliance portions can be detachably linked to the adjacent (mesial) end portions of the lateral sections in a manner that permits relative upward and downward movement of the linked end portions, but that restricts relative lateral movement of the linked end portions to thereby restrict the drift or lateral movement of the anterior teeth at the distal ends of the anterior appliance section relative to the posterior teeth at the mesial ends of the posterior appliance sections.

As a specific example, at the adjacent end portions (interproximal wall end portions) of a posterior appliance portion or section and the anterior appliance portion or section, an interlocking joint can be provided that permits upward and downward movement of at least one of the adjacent appliances end portions, but restricts or prevents lateral movement of such end portions and the teeth overlaid by such end portions. Thus, the mesial wall or end of each posterior appliance section and adjacent distal end of the anterior appliance section can be provided with the interlocking joint.

In one form, the interlocking joint comprises a projection at the end of one of the adjacent posterior and anterior appliances portions and an upright receiving slot can be provided at the end of the other of the adjacent posterior and anterior appliance ends. By positioning the projection within the slot, the relative lateral motion of the adjacent ends is restricted or prevented, thereby restricting or preventing the lateral movement of the anterior and posterior teeth covered by the anterior and posterior appliances portions; but the projection can desirably slide relative to the slot to relieve stress on the appliance portions at their joint during, for example, chewing by the user.

In addition, desirably the appliance portion with the slot remains a separate element from the appliance portion with the projection so that the slotted portion can be lifted upwardly and removed from the user's mouth separately from the other appliance portion with the projection. If there are two posterior appliance portions and one anterior appliance portion with adjacent or interproximal ends, this interlocking structure can be provided at each set of adjacent end portions. In a specific example, the interlocking structure can comprise a dove tail joint with a tenon portion comprising the projection and a mortise portion comprising the slot. The tenon can be flared to engage end or interproximal walls defining the slot to hold the interlocking joint together while still permitting upward movement of one or both of the appliance portions relative to one another.

In addition, the slot can be oriented to be parallel to the draw or angular inclination (e.g., the posterior teeth are angled lingually and the slot can be oriented to be parallel to the angle of inclination of the canine tooth at the interproximal end of the posterior appliance portions adjacent to the interproximal end of the adjacent anterior appliance portion). The slot can be open at the top to permit either appliance portion to be moved upwardly (with the projection sliding relative to the slot) and removed from the user's mouth. The occlusal surface of the projection can be positioned and shaped to match the occlusal surface of the opposed tooth. Alternatively, the slot can be closed at the top; in which case the appliance portion with the slot can be moved upwardly to clear the slot and the user's mouth prior to removing the appliance portion with the projection.

Depending on the treatment objective, the appliances can be worn with either one or two posterior sections or all three sections: one anterior and two posterior sections on either maxillary or mandibular teeth, which ultimately alters the user's occlusion temporarily, resulting in improved jaw position and/or dental aesthetics. When wearing the appliance sections, the patient may have relief from TMJ related symptoms (e.g., tension headaches, TMJ noise and pain, cervical muscle discomfort, mastication dysfunction, craniomandibular dysfunction), or may have improved facial symmetry and appearance.

In accordance with an embodiment, a plural section dental appliance for occupying the measured intra-occlusal space between opposed upper and lower pairs of teeth of a user of the appliance is disclosed. The measured intra-occlusal space is the distance between the opposed upper and lower teeth when the user's mandible is in a physiologic rest or relaxed position minus a freeway space. The freeway space is determined based on the providers design and ranges from 1 mm to 3.5 mm, with a desirable range being equal to, substantially equal to or identical to from 2 to 3 mm.

In accordance with an embodiment, the plural section dental appliance comprises: a front or anterior portion or section having a front body that defines anterior teeth receiving pockets adapted to receive and engage the anterior teeth of the user. The anterior teeth of the user in this disclosure are the upper or lower incisors and optionally the upper or lower incisors and upper or lower canine teeth of the user if the front appliance portion is designed to include a pocket for the canine teeth. The front body comprises an occlusal portion having a thickness that substantially occupies the measured intra-occlusal space between the upper and lower anterior teeth of the user. The plural section dental appliance can also comprise a first lateral portion having a first lateral body that defines pockets that are adapted to receive and engage the upper or lower posterior teeth of the user at a first side of the user's mouth. The posterior teeth are the pre-molar and molar teeth of the user, and optionally the canine teeth. Depending upon how the anterior and posterior appliance sections are designed, the canine teeth can be engaged and covered by the anterior appliance section, in which case the canine teeth are included in the definition of anterior teeth; or one or both canine teeth can be engaged and covered by a respective posterior appliance portion, which case the covered canine tooth or teeth are included in the definition of posterior teeth. The first lateral body comprises a first lateral body occlusal portion having a thickness that substantially occupies the measured intra-occlusal space between the upper and lower posterior teeth (e.g., the canine teeth, pre-molars and molars) at the first-side of the user's mouth. The plural section dental appliance can also comprise a second lateral portion having a second lateral body that defines pockets that are adapted to receive and engage the upper or lower posterior teeth of the user at a second side of the user's mouth opposite to the first side of the user's mouth. The second lateral body comprises a second lateral body occlusal portion having a thickness that substantially occupies the measured intra-occlusal space between the upper and lower posterior teeth (e.g., the canine teeth, pre-molars and molars) at the second side of the user's mouth. In addition, the front body has first and second front body end portions, which can be referred to as first and second front body distal end portions. The tooth receiving pocket at the first front body or first distal end portion receives the distal most anterior tooth (the canine tooth or distal most incisor) at the first side of the user's mouth. The tooth receiving pocket at the second front body or second distal end portion receives the distal most anterior tooth (the canine tooth or distal most incisor) at the second side of the user's mouth. In addition, the first lateral body has first and second lateral body end portions, the first body end portion being at the mesial end of the first lateral body. In addition, the second lateral body has third and fourth lateral body end portions, the third lateral body end portion being at the mesial end of the second lateral body. The pocket at the first lateral body or first distal end portion being adapted to engage the forward most tooth of the posterior teeth at the first side of the user's mouth (the user's canine tooth at the first side of the user's mouth if this canine tooth is included as one of the posterior teeth in the first lateral appliance section or the anterior most premolar tooth at the first right side of the user's mouth if this canine tooth is included as one of the anterior teeth in the front appliance section). The pocket at the second lateral body or second distal end portion being adapted to engage the forward most tooth of the posterior teeth at the second side of the user's mouth (the user's canine tooth at the second side of the user's mouth if this canine tooth is included as one of the posterior teeth in the first lateral appliance section or the anterior most premolar tooth at the second side of the user's mouth if this canine tooth is included as one of the anterior teeth in the front appliance section). In accordance with this embodiment, when the appliance is worn by a user, the first front or first distal end portion of the front body is positioned adjacent to the first lateral body end portion or mesial end portion of the first lateral body and the second front or second distal end portion of the front body is positioned adjacent to the second lateral body end portion or mesial end portion of the second lateral body. In addition, in this embodiment the first front body end portion-is movable relative to the first lateral body end portion and the second front body end portion is movable relative to the third lateral body end portion.

In accordance with an embodiment, a plural piece dental appliance is disclosed for occupying the measured intra-occlusal space between opposed upper and lower pairs of teeth of a user of the appliance, the measured intra-occlusal space being the distance between the opposed upper and lower teeth when the user's mandible is in a-rest or relaxed position minus the freeway space, the embodiment of dental appliance comprising: a front or anterior portion adapted to engage the upper or lower anterior teeth of the user, the anterior teeth being the incisors or sometimes the incisors and canine teeth of the user, the front portion comprising a front body portion comprising a contiguous front wall comprising a front wall interior surface adapted to engage the facial surfaces of the engaged upper or lower incisors of the user and an opposed front wall exterior surface, the front body portion comprising a contiguous rear wall comprising a rear wall interior surface adapted to engage the lingual surfaces of the engaged upper or lower anterior teeth (the incisors or incisors and canine teeth) of the user and a rear wall exterior surface adapted to face the tongue of the user, the front portion also comprising a front occlusal wall portion extending between the front wall and the rear wall, the front occlusal wall portion comprising a front occlusal wall interior surface adapted to engage the occlusal surfaces of the engaged upper or lower incisors of the user, the front occlusal wall portion comprising a front occlusal wall exterior surface adapted to face the occlusal surfaces of the teeth of the user opposed to the teeth of the user engaged by the front wall portion, the front occlusal wall having a thickness between each pair of opposed teeth that is substantially equal to a measured intra-occlusal space between the respective pairs of opposed anterior teeth engaged by the front portion, the front body portion also comprising a first front body end portion or first distal end portion and a second front body end portion or second distal end portion; a first lateral portion adapted to engage the posterior teeth at a first side of the mouth of the user (these posterior teeth being the upper or lower canine, pre-molar and molar teeth of the user at the first side of the user's mouth or the upper or lower pre-molar and molar teeth of the user at the first side of the user's mouth if the canine teeth are included in the front appliance portion), the first lateral portion comprising a first lateral body portion comprising a contiguous first buccal wall comprising a first buccal wall interior surface adapted to engage the buccal facial surfaces of the teeth engaged by the first lateral portion and an opposed first buccal wall exterior surface facing the cheeks at the first side of the user's mouth, the first lateral portion comprising a first lingual wall-comprising a first lingual wall interior surface adapted to engage the lingual surfaces of the teeth engaged by the first lateral portion and a lingual wall exterior surface adapted to face the tongue of the user, the first lateral portion also comprising a first-occlusal wall portion extending between the buccal wall and the first lingual wall, the first occlusal wall comprising a first occlusal wall interior surface adapted to engage the occlusal surfaces of the teeth of the user engaged by the first-lateral portion, the first-occlusal wall portion comprising a first occlusal wall exterior surface facing the occlusal surfaces of the teeth of the user opposed to the teeth of the user engaged by the first lateral portion (opposing dentition) the first occlusal wall having a thickness between each pair of opposed teeth that is substantially equal to the measured intra-occlusal space between respective pairs of teeth engaged by the first lateral portion, the first lateral body comprising a first lateral body end portion or first mesial body end portion and a second lateral body end portion; a second lateral portion adapted to engage the posterior teeth at a second side of the mouth of the user opposite to the first side (these posterior teeth being the upper or lower canine, pre-molar and molar teeth of the user at the second side of the user's mouth or the upper or lower pre-molar and molar teeth of the user at the second side of the user's mouth if the canine teeth are included in the front appliance portion), the second lateral portion comprising a second lateral body portion comprising a contiguous second buccal wall comprising a second buccal wall-interior surface adapted to engage the buccal facial surfaces of the teeth engaged by the second lateral portion and an opposed second buccal wall exterior surface facing the cheeks of the user at the second side of the user's mouth, the second lateral portion comprising a second lingual wall comprising a second lingual wall interior surface adapted to engage the lingual surfaces of the teeth engaged by the second lateral portion and a second lingual wall exterior surface adapted to face the tongue of the user, the second lateral portion also comprising a second occlusal wall portion extending between the second buccal wall and the second lingual wall, the second occlusal wall comprising a second occlusal wall interior surface adapted to engage the occlusal surfaces of the teeth of the user engaged by the second lateral portion, the second-occlusal wall portion comprising a second occlusal wall exterior surface facing the occlusal surfaces of the opposing teeth of the user opposed to the teeth engaged by the second lateral portion, the second occlusal wall having a thickness between each pair of opposed teeth that is substantially equal to a the measured intra-occlusal space between respective pairs of teeth engaged by the second lateral portion, the second lateral body comprising a third lateral body end portion or mesial body end portion and a fourth lateral body end portion; the first front body end portion or first distal end portion being adapted to be positioned adjacent to the first lateral body end portion or mesial end portion of the first lateral body and the second front body end portion or second distal end portion being adapted to be positioned adjacent to the third lateral body end portion or the mesial end portion of the second lateral body when the front body portion, and first and second lateral portions are worn by a user. In addition, all sections of the appliance can be removed relative to one another. Moreover, in accordance with an embodiment, the first front body end portion is movable relative the first lateral body end portion and the second front body end portion is movable relative to the third lateral body end portion when worn by a user.

As yet another aspect of embodiments, the front or anterior body portion can comprise an occlusal portion having a thickness that is equal to the measured intra-occlusal space between the upper and lower incisors of the user, the first lateral body portion comprising a first lateral body occlusal portion having a thickness that is equal to the measured intra-occlusal space between the upper and lower posterior teeth (e.g., between the canine teeth, pre-molars and molars at the first side of the user's mouth, the second lateral body portion comprising a second lateral body occlusal portion having a thickness that is equal to a the measured intra-occlusal space between the posterior teeth (e.g., between the upper and lower canine teeth, pre-molars and molars) at the second side of the user's mouth.

In accordance with an aspect of embodiments, the first front body end portion or first distal end portion can be removed independently from the first lateral body end portion and the second front body end portion can be removed independently from the third lateral body end portion. The front or anterior appliance portion or section and the first and second lateral appliance portions or sections can be completely separate appliances-and therefore, can be worn by the user individually or as a combination depending on the treatment protocol. In some cases, the patient has a collapsed bite or severe curve of spee only on one side of the dental arch which leads to ipsilateral compression of the condyle and deviation of the mandible on that side. The plural sectional piece design of this appliance allows the provider to add occlusal height to the ipsilateral compressed side only, correcting the mandibular compression on the problem side. This much needed feature is not currently available with the one piece occlusal appliance that span over the entire dental arch.

As another aspect of embodiments, the first front body end portion can abut the first lateral body end portion and the second front body end portion can abut the third lateral body end portion when the dental appliance sections are worn by the user. Thus, the distal end walls of the front or anterior body can abut the respective adjacent mesial walls of the first and second lateral body portions when the dental appliance is worn by the user.

In accordance with further aspects of an embodiment, a void can be provided at each of first and second front body end portions and at each of the first and third lateral body end portions.

As a further aspect of embodiments, the second body end portion can be adapted to surround a molar of the user at the first side of the user's mouth when the first lateral portion is worn by the user and the fourth body end portion can be adapted to surround a molar of the user at the second side of the user when the second lateral portion is worn by the user.

As a further aspect of embodiments, the front portion and first and second lateral portions can each be each adapted for mounting to and engagement by respective lower teeth of the user.

As yet another aspect of embodiments, the front and rear walls of the front or anterior appliance portion can be of a uniform thickness and first and second buccal walls and first and second lingual walls of the lateral portions can be of a uniform thickness.

As still further aspects of embodiments the thickness of the walls of the appliances can be thin, such as from 0.3 to 0.6 mm thick.

As a still further aspect of embodiments, a first link can be provided to interconnect the first front body end portions and the first lateral body end portion and a second link can be provided to interconnect the second front body end portion and the third lateral body end portion; the first and second links allowing relative upward and downward movement of the interconnected body end portions.

In accordance with another embodiment of this disclosure, a method of customizing a dental appliance for a user is disclosed and comprises: determining a rest or relaxed position of the user's mandible; obtaining a bite registry of a measured intra-occlusal space the user's upper and lower teeth when the patient's mandible is in the rest position; preparing a mold or a digital representation of the user's upper and lower teeth; preparing front and first and second lateral appliance components, if all such appliance portions are being used for a particular patient; the front appliance component having a front body shaped to engage the respective front teeth of the user; the first lateral appliance having a first-lateral body shaped to engage the teeth of the user at a first-side of the user's mouth; the second-lateral appliance component having a second lateral body shaped to engage the teeth of the user at a second side of the user's mouth opposite to the first side of the user's mouth; the first and second lateral appliance components each having an occlusal portion of a thickness in the region of each pair of opposed teeth that is substantially equal to the measured intra-occlusal space between the opposed pair of teeth; and wherein the front appliance component, the first lateral appliance component and the second lateral appliance are movable relative to one another. In accordance with this method, front and first and second lateral appliances components can be separate disconnected components; which can be used as any combination or individually based on the treatment needs.

The foregoing and other objects, features, and advantages of the invention will become more apparent from the following detailed description, which proceeds with reference to the accompanying figures. It is to be understood that the invention includes all of the novel and non-obvious elements and method acts disclosed herein both individually and in all combinations and sub-combinations thereof.

BRIEF DESCRIPTION OF THE DRAWINGS

FIG. 4 is a top exterior view of an exemplary appliance using a three piece combination of appliance sections that has been fabricated to form-fit the lower dentition of FIG. 1.

DETAILED DESCRIPTION

Figure 1:
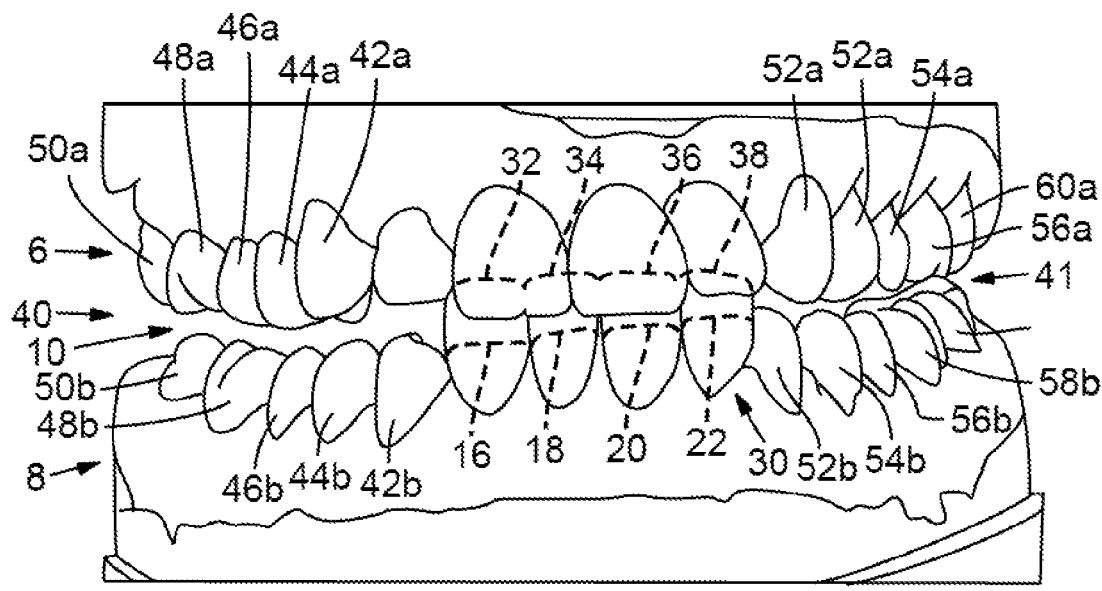
FIG. 1 is a model of an exemplary patient or appliance user's upper jaw and upper teeth or dentition together with the individual's lower jaw and lower teeth or dentition, and with the lower jaw positioned as if the user's lower jaw were in a relaxed state. For purposes of this description, models of a user's mouth illustrate the user's mouth and are used for convenience.

This disclosure relates to a sectional dental appliance that is typically prepared by a lab from a mold prepared by a licensed dentist or other authorized professional. The mold is prepared following relaxation of a patients jaw to a natural relaxed position, and determining the intra-occlusal space when the jaw is in this relaxed position. The relaxed position refers to the position of the jaw following relaxation of the jaw muscles by a relaxation procedure. The intra-occlusal space is the space between opposed upper and lower teeth of the patient, minus a freeway space between various adjacent upper and lower teeth, when the lower jaw is in a relaxed position. One desirable freeway space is equal to, substantially equal to, or identical to 2 mm to 3 mm. A sectional appliance is made to cover selected teeth of the user with the thickness of the occlusal portion of the appliance overlaying each covered occlusal tooth surface being equal to, substantially equal to, or identical to the measured intra-occlusal space between the occlusal surfaces of each covered tooth and the adjacent upper or lower tooth when the jaw is in a relaxed position As a result, when the appliance is worn, the user's jaw is supported at a relaxed position when the user's teeth mesh together, such as during chewing or swallowing. The device, when worn, can increase the patient's vertical dimension of occlusion and thereby augments the position of the user's jaw to achieve the intended use; this results in a desirably aesthetic alignment and symmetry of the face, as well as stretching and smoothing the skin of the user.

The dental appliance desirably comprises first and second, lateral or posterior portions, one for the left side of a user's mouth and one for the right side of the user's mouth. The posterior portions each desirably cover a majority, and more desirably all, of the posterior teeth, and corresponding dentures or partials if present, of the user when worn; but not the user's incisors. The user's posterior teeth are the molars, bicuspids (pre-molars) and optionally the canine teeth (the canine teeth being included in the posterior teeth if not included in the section of an appliance that covers the anterior teeth). An optional and desirable anterior or front piece or portion of the dental appliance, if included, desirably covers the user's anterior teeth of the upper or lower jaw. The user's anterior teeth are the incisors and optionally the canine teeth (the canine teeth being included in the anterior teeth if not included in sections of the appliance that covers the posterior teeth. In one desirable embodiment, the posterior teeth include the molars, pre-molars and canine teeth and the anterior teeth are the incisal teeth. Teeth on either side of the arch often have different angulations and different line of draw due to their lingual or buccal inclination. The use of a sectional appliance (with two or three piece appliance sections) that can draw from groups of teeth independently reduces stress on the appliance as well as reducing torque on the user's dentition that would otherwise be present if the appliance were made in the form of a one piece appliance spanning over the entire dental arch. Also, a plural piece design is easier to remove and clean and facilitates dental hygiene. The plural piece design also solves the problem of bulkiness and invasion of tongue space which is common with one piece full arch occlusal appliances because the appliance portions or sections of a plural section design can have relatively thin lingual walls. The plural pieces of the sectional appliance can be made for the user's upper or lower detention, or one or more sections for the upper detention and one or more sections for the lower dentition using the approach described above. The appliance can be used in any combination for the top or bottom teeth depending on the intended use.

The appliance sections or components are desirably made to fit and cover either the upper or lower teeth of the user; or most desirably the lower teeth of a user with no components covering teeth of the upper jaw of the user. Again, the thickness of the appliance, between interior and exterior occlusal surfaces of the appliance, which can be called the intra-occlusal space or make-up distance between adjacent teeth, is equal to or identical to, or substantially equal to the distance between the teeth minus the freeway space for function, when the jaw is in a relaxed position.

In cross section, the appliance portions are desirably u-shaped and desirably have an occlusal surface that conforms to the shape of the occlusal surface of the opposed teeth so that when worn, the occlusal surface of the appliance portions and of the teeth opposed to the appliance portions so that the appliance portions facilitate use during chewing. The appliance portions have walls with the interior (lingual) and exterior (facial including buccal and labial) surfaces of the teeth that conform to such respective teeth surfaces so that the appliance is held in place by the teeth. Less desirably, the appliance components can be made to only cover the upper teeth. A still less desirable alternative is to have the appliance components cover adjacent upper and lower teeth with the intra-occlusal thickness being made up partially by the upper and partially by the lower of the adjacent appliance component while leaving the freeway space between the opposed teeth. Combinations of upper and lower appliance components can also be used for a given user. However, the most desirable embodiment of the appliance has only first and second separate posterior or lateral portions or components mounted to or carried by the lower teeth, with or without a third front or anterior appliance portion or component only on the lower front teeth of the user. The appliance can be worn with one or plural sections on either top or bottom teeth to improve the user's jaw position, dental aesthetics and potentially provide relief to TMJ related symptoms (e.g., tension headaches, TMJ noise and pain, cervical muscle discomfort, mastication dysfunction, craniomandibular dysfunction), as well as improving facial symmetry and appearance.

The appliance may be affixed to the user's teeth, such as temporarily held in place such that it is removable. The appliance can, for example, desirably be temporarily held in place by either mechanical retention (e.g., resilient snap fitting on teeth, with a portion of the device extending below the inwardly extending clinical crown of the tooth or with portions of the appliance extending between gaps between adjacent teeth) or by applying temporary dental adhesives. Examples of desirable temporary adhesives are previously FDA (United States Federal Drug Administration) approved denture adhesives such as sold under the trademarks Poligrip® or Fixodent® by Proctor & Gamble Company, or temporary dental adhesives such as sold under the brand name Temp Bond® Clear by Kerr Corporation.

In a desirable approach, the appliance is made of a material that is durable and that has sufficient flexibility to allow the spreading of the sides of each appliance component sufficiently to allow removal of the appliance components from the user's mouth, such as for cleaning. Final fitting of the appliance can be accomplished locally, such as at a dentist's office, following the manufacturing of the appliance. Also, the appliance may be made as a temporary appliance while waiting for a more durable finished appliance or to allow the user to wear the appliance for a period of time to determine whether further adjustments (e.g., in make-up bite distances) before a more durable or permanent restoration (such as crowns or veneers) is made and provided to the user.

The dental appliance can be designed to be fully anatomical, tooth colored and removable; such as of two or three pieces. As explained above, the appliance desirably includes two posterior or lateral sections or portions that desirably cover the posterior teeth (the molars and bicuspids, with or without the canine teeth) of a user and can also include one anterior or front section or portion that covers the anterior teeth (the incisal teeth, with or without the canine teeth) of the user.

In a typical manufacturing approach, a dentist or other individual provides a digital (e.g., 3-D digital scan) or physical (e.g., of polyvinyl) impression of upper and lower teeth of a user for whom the appliance is being prepared. A dental model of the user's maxillary and mandibular dentition is made from this 3-D digital scan or impression, or otherwise. For example, a record of the user's full detention in both upper and lower dental arches is can be obtained using an impression tray that does not touch any tooth structure, thus forming an accurate dental impression of all tooth surfaces, including the facial, buccal and lingual tooth surface. This can be done by taking polyvinyl siloxane dental impressions or a 3D digital scan of the dental arch or the patient's full dentition. Authorized individuals such as dentists, and denturists (if permitted) or others as permitted by governmental regulations can prepare such molds or dentition records.

The appliance is desirably designed to support the occlusion (while having a freeway space, for example two to three millimeters) in a relaxed state, such as the physiologic rest position, of the lower jaw muscles. The rest position or relaxed position is the position of the mandible when the patient is resting in an upright position following a jaw muscle relaxation treatment. One desirable relaxed state is with the condyles are in a neutral unrestrained position in the mandibular fossa. In this position, the various mandibular muscles are simultaneously at their resting length and in balanced tonus with one another. A rest position for the jaw is determined with the patient or user in an upright sitting postural position. In this position the patient: (a) is sitting with head and back straight in a straight back chair; (b) has both feet flat on the floor; (c) has both hands resting in his or her lap; and (d) is breathing deeply with jaw muscles relaxed to a rest or relaxed position. The freeway space is the space between the occluding surfaces of adjacent maxillary and mandibular teeth which is needed for function. The freeway space allows for proper function and mastication. The intra-occlusal space is measured by subtracting the freeway space from the occlusal space between the teeth when the user's mandible is in a relaxed position. The intra-occlusal space is different for each user and can be measured by the provider following a relaxation treatment selected by the provider.

The rest position of the mandible can be achieved using any suitable relaxation technique by the provider. One such technique is as using ULF-TENS stimulation. Another suitable technique is providing a deep massage of the posturing muscles of the mandible. When in a relaxed position, the mandible typically rises about one to two millimeters from its rest position with application of ULF-TENS stimulation. The intra-occlusal space (which determines the occlusal thickness of the appliance) is measured by subtracting the freeway space from the occlusal space between opposed teeth in the relaxed position of the mandible.

In one exemplary approach, a relaxed or mandibular rest position can be achieved by the application of Ultra Low Frequency Transcutaneous Electrical Neural Stimulation (ULF-TENS) such as by using Federal Drug Administration (FDA) approved ultra-low frequency transcutaneous Electrical Neural Stimulation (Ulf-TENS) to the facial and head and neck muscles to allow the posturing muscles of the mandible to position the mandible to a relaxed position. An exemplary ULF-TENS treatment to achieve a desirable relaxed position, although variable in duration, is from thirty to sixty minutes, using, for example, a J5 Myomonitor from Myotronics-Noromed, Inc. Stimulation of the muscles with ULF-TENS contracts and repetitively relaxes the masticatory muscles, such as every 1.5 seconds, to help the muscles relax and achieve a desired relaxed position of the mandible. U.S. Pat. No. 7,844,340 describes an exemplary ULF-TENS treatment approach and is incorporated by reference herein. Desirably the relaxation treatment is performed until the mandible remains in an equal, substantially equal, or identical position in response to additional treatment.

The positioning of the mandible in a relaxed position can be visually observed or otherwise determined. In one approach, electrosonography (ESG) measurements or surface electromyography (s-EMG) measurements can be made to verify the positioning mandible in the relaxed position. These measurements can be repeated and compared until the measurements indicate the relaxed position has been achieved (e.g., the measurements remain equal, substantially equal or identical in response to additional treatment. Muscles that are in spasm (unrelaxed) show elevated EMG's. For example, Table 1 below shows a comparison of average s-EMG measured electrical signals, in microvolts over fifteen second intervals, determined for left and right masseter (LMM and RMM); left and right temporalis anterior (LTA and RDA); left and right anterior digastric (RDA and LDA); and left and right cervical group (LCG and RCG) muscles for a person in an unrelaxed mandibular state (on the left in Table 1) and in the physiologic rest position (on the right in Table 1). These measurements were obtained using eight channel electromyographic equipment using surface electrodes affixed by adhesive tape to the person's skin with the electrodes positioned bilaterally and parallel to the muscle fibers.

TABLE 1

Surface Electroyography (sEMG) measurements prior to ULF-TENS treatment on the left and after ULF-TENS treatment on the right.

| Sample-15.00 seconds | | Sample-15.00 seconds | |
|---|---|---|---|
| LTA (Left Temporalis Anterior) | Avg. = 7.1 uV | LTA (Left Temporalis Anterior) | Avg. = 2.6 uV |
| RTA (Right Temporalis Anterior) | Avg. = 7.1 uV | RTA (Right Temporalis Anterior) | Avg. = 1.2 uV |
| LMM (Left Masseter) | Avg. = 1.9 uV | LMM (Left Masseter) | Avg. = 1.3 uV |
| RMM (Right Masseter) | Avg. = 5.1 uV | RMM (Right Masseter) | Avg. = 0.7 uV |
| LCG (Left Cervical Group) | Avg. = 5.7 uV | LCG (Left Cervical Group) | Avg. = 2.2 uV |
| RCG (Right Cervical Group | Avg. = 11.5 uV | RCG (Right Cervical Group | Avg. = 2.0 uV |
| LDA (Left Digastric) | Avg. = 28.2 uV | LDA (Left Digastric) | Avg. = 0.9 uV |
| RDA (Right Digastric) | Avg. = 30.9 uV | RDA (Right Digastric) | Avg. = 0.9 uV |

Often times, after a relaxation treatment, the muscles that are attached to the TMJ disk relax and allow the TMJ disk to move to the ideal spot in the joint. Many times patients report less joint pain when the TMJ joint is in this position and the popping and clicking noise of the TMJ goes away or is substantially reduced. Less noise in the electrosonography report indicates improved disk position. The improved mandibular range of motion can also be recorded subjectively. The range of motion of the mandible can be measured before and after relaxation by either measuring maximum opening or by measuring lateral deviation with a Boley gauge or it can be recorded, such as by any FDA approved computerized jaw tracking equipment.

With the muscles of the mastication are in a relaxed position, a measurement or determination (e.g., physical measurement, digital or other capture of information) is made of the distance between various adjacent upper and lower teeth (e.g., all of the teeth or the teeth to be covered by the sectional appliance). The intra-occlusal space (the distance in the relaxed state of mandible minus the freeway space) is desirably correlated to anatomical features or landmarks of the teeth that are also present in the dental impressions or 3D digital scans. That is, a bite registration of the user is obtained of these intra-occlusal spaces that, if occupied by the thickness of the occlusal surface of the appliance portions, will support the facial and jaw muscles of the user in the relaxed position. The bite registration that is obtained by the provider can be digital or physical using polyvinyl impression material.

One exemplary procedure is to make a mark on a user's nose and chin prior to relaxing the lower jaw to a relaxed mandibular position. When the user's lower jaw is in a mandibular relaxed position, the distance between the dots is measured (e.g., using a caliper) to indicate the user or patient's rest position (PRP). The caliper setting can then be reduced by the desired freeway space between the occlusal surfaces of opposed teeth, for example between 2 mm and 3 mm. Bite registration material, such as polyvinyl siloxane, can be placed in the user's mouth with the user closing his/her mouth until the PRP minus freeway space setting is reached. This position is held until the bite registration material is set. The thickness and shape of the bite registration material (make-up bite information) between two adjacent teeth corresponds to the thickness and shape of that portion (the occlusal portion) of the dental appliance to be positioned in the teeth to support the lower jaw in the PRP position or relaxed position minus the freeway space. One way to check for the relaxed position is to have the patient open and close on the purposed bite registration to check for improvement in the joint noise and range of motion of the mandible.

The make-up bite information (digitally or in the form of a bite registration) is sent with the mold (digital or physical mold) to a dental lab (or other approved facility) which then makes the appliance with the thickness of the occlusal portions of the appliance to be positioned between the user's opposed pairs of teeth equal to, substantially equal, and most desirably identical to the make-up bite distance. Alternatively, a dentist or other authorized professional may have the capability of making the appliance in, for example, their own office.

The appliance sections or portions that comprise the appliance for a particular user can be fabricated to the desired fit for the user, such as by milling FDA approved materials. Less desirably, the appliance portions can be molded. Exemplary suitable materials include PMMA (Poly Methyl Methacrylate), acrylic resin, lithium disilicate, Zirconia and acetal resin. A suitable PMMA is a bisphenol A free PMMA product sold in solid disk form by Talladium, Inc. of Valencia, Ca. under the brand name Luminesse. Other materials suitable for intra-oral dental use may also be used.

Examples of current 3D milling machines that are capable of fabricating anatomical tooth colored appliances include milling machines made by the following companies: Amann Girrbach, Roland, and the Zirkonzahn. These precision CAD CAM milling machines are currently used for manufacturing appliances in the dental industry. The appliance sections are desirably made with material added to the appliance to fill the intra-occlusal space that is present when the muscles are relaxed, minus the freeway space. One desirable exemplary material for the appliance components is poly (methyl methacrylate), also called PMMA or acrylic or acrylic glass. The appliance components can be of a monolithic material and need not use a metal platform similar to a partial denture design. The selected material can be tooth colored, which can appear like veneers or on-lays, making the appliance components both aesthetic and functional. The appliance is desirably delivered like an overlay on the existing dentition without the need to alter the existing tooth structures. The material can be added to, if further adjustments to the appliance or change of thicknesses is desired during final fitting of the appliance portions to the user.

Once fabricated, the final fitting of the appliance can be performed at the prescribing dentist's or other professional's office. For example, the appliance sections can be ground to adjust the user's bite. Desirably, without requiring any alterations to the user's existing dentition, the appliance can be delivered in sections as an overlay and secured with built in mechanical retention and/or adhesive retention.

Therefore, the actual dimensions of the appliance is customized for the user and will depend upon the patient's anatomy and is typically different for each patient. The dimensions of the bite adjustment portion of the appliance are based on the final relationship of the maxilla (upper jaw) to the mandible (lower jaw) at the relaxed position of the mandible.

The use of a plural piece appliance allows the appliance to be thinner than if the appliance were of one piece, which would require the appliance to be bulkier to withstand pressure on the appliance. For example, the disclosed appliance components can have side walls adjacent to the lingual surfaces (and facial surfaces) of the teeth that are as thin as 0.3 mm, with a desirable thickness of such sidewalls being less than 0.6 mm and a desirable range of such side wall thicknesses being from 0.3 mm to 0.6 mm and more desirably from 0.4 mm to 0.6 mm. Also, a plural piece appliance is easier to remove as it is less affected by undercuts and tooth crowding that exists in the teeth of many patients. A bulky appliance would occupy too much tongue space and make it difficult for the user to speak or chew with the appliance in place. If such a user were to remove the orthotic to bite on the existing dentition, the jaw muscles would tend to go into spasm to accommodate to the patient's original bite. A plural portion appliance design (front and first and second lateral portions) facilitates modeling of the user's mouth and makes it easier to fit the appliance to the user.

The plural section design of the appliance can potentially provide a template for an orthodontist or the restorative dentist to use as a reference for most comfortable position of the mandible. The appliance can be easily sectioned to smaller pieces and removed from the mouth strategically during the above mentioned treatments. Currently there is no such removable appliance known to the inventor to support this treatment technique.

The disclosed appliance is functional, meaning that the patient can chew and function with it in place as the appliance components look and feel like teeth, as well as its unique feature of being secured to teeth with temporary adhesive. The appliance, when worn by the user for which it is designed, maintains and supports the balanced state of the facial muscles of the user, during chewing, swallowing and other functions to in effect provide the user with a new purposed biting surface. By providing appliance portions with an interior occlusal surface that substantially matches or matches the exterior surface of the covered teeth and with an exterior occlusal surface that matches the occlusal surfaces of the opposed uncovered teeth of the user, the appliance is functional in that facilitates effective chewing by the user. The disclosed appliance components can be worn during the day as a removable appliance. They can also be adhered to the teeth temporarily, with any FDA approved temporary dental cement, for more stability during chewing or for night time wear. When the appliance is worn, the user exhibits relaxed facial muscles as well as tighter facial skin, contributing to a more youthful appearance. Also, the make-up bite adjustment provided by the appliance can be established so as to correct an undesired overly asymmetric facial appearance (e.g., by increasing the bite adjustment on one side of the user's face as compared to the bite adjustment at the other side of the user's face). The appliance device increases the patient's vertical dimension of occlusion to a position where the user has a more comfortable bite. Because of the non-invasive and removable nature of desirable embodiments, the overall effects of wearing the appliance are reversible.

FIG. 1 is a model of an individual's upper jaw 6 and upper teeth together with the individual's lower jaw 8 and lower teeth, and with the lower jaw positioned as if the user's lower jaw were on physiologic trajectory supporting the lower jaw in a relaxed in response to a relaxation treatment, such as an ULF-TENS treatment. In this state, one can see that there is a gap 10 between adjacent upper and lower teeth, such as between molar 48a of the upper jaw and molar 48b of the lower jaw. In FIG. 1, the dotted lines indicated at 16, 18, 20 and 22 represent the position of the individual's actual lower front (incisor) teeth in the model. In FIG. 1, a front portion or section of an appliance is indicated generally at 30 and is coupled to and receives the front incisor teeth of the user. The front appliance portion adds height to the height of the respective front teeth to elevations indicated respectively at 32, 34, 36 and 38. Thus, as shown in FIG. 1, the front appliance portion 30 closes the gap or (intra-occlusal space) between the lower front teeth of the user and the upper front teeth that would otherwise exist when the lower jaw is in a relaxed position. Therefore, the appliance 30 will hold the upper and lower jaws relative to one another in the relaxed state (minus the freeway space) when the front portion of the appliance is in position and the user's teeth mesh.

In FIG. 1, at a first side 40 of the user's upper and lower jaws, upper and lower canine teeth 42a and 42b, upper and lower bicuspids or pre-molars 44a, 44b and 46a, 46b; and upper and lower first and second molars 48a, 48b and 50a, 50b, are shown. The third molars or wisdom teeth are missing in this model. In addition, at a second side 41 of the user's upper and lower jaws, upper and lower canine teeth 52a and 52b, upper and lower bicuspids or pre-molars 54a, 54b and 56a, 56b; and upper and lower first and second molars 58a, 58b and 60a, 60b, are shown.

Figure 1A:
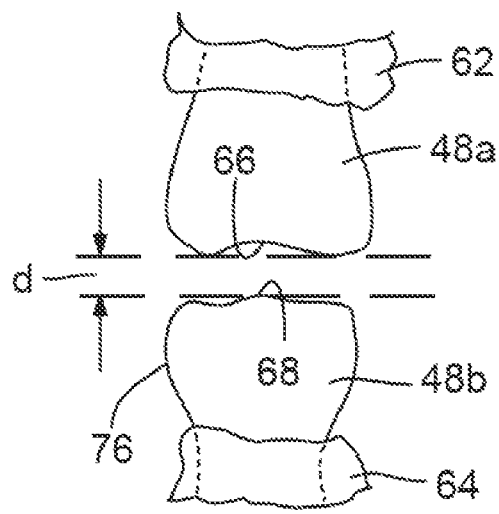
FIG. 1A illustrates a single pair of opposed teeth and shows the measured intra-occlusal space between the occlusal surfaces of these teeth, when the mandible supporting the lower tooth is in a rest position; the intra-occlusal space is exaggerated in FIG. 1A for purposes of illustration.
Figure 1B:
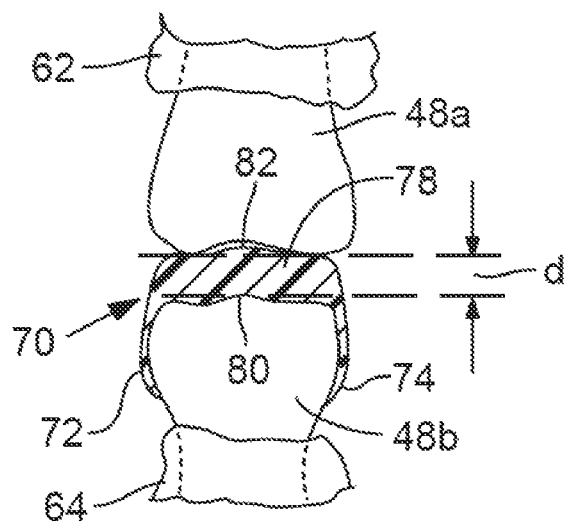
FIG. 1B illustrates the teeth of FIG. 1A with portion of a dental appliance shown mounted to the lower tooth and with an occlusal section of the appliance filling a measured intra-occlusal space between the illustrated pair of teeth (the measured occlusal space between the other pairs of teeth of the upper and lower dental arches would also be filled by the appliance to support the mandible in a rest position and provide an improved occlusion when the teeth articulate).

FIG. 1A illustrates the teeth 48a and 48b surrounded by portions of the user's upper and lower gums 62, 64 and also illustrating an exemplary intra-occlusal space d between the facing occlusal surfaces 66, 68 of these teeth. The space d is the distance between these occlusal surfaces that mimics the intra-occlusal surface measured by the provider with the lower jaw in a relaxed position and subtracting out the freeway space, and captured with digital or physical bite registration material for the purpose of communication to a laboratory or other facility where the appliance is to be made. FIG. 1B illustrates a portion 70 of a first posterior or lateral appliance side portion. The portion 70 includes first and second side walls 72, 74 (side wall 72 being the buccal side wall and side wall 74 being the lingual side wall). The illustrated side walls extend downwardly to a location below the height of contour of the clinical crown 76 of the tooth 48b. The appliance portion 70 comprises an occlusal portion 78 that extends between the side walls 72, 74. The occlusal portion has an interior occlusal surface 80 shaped to conform to the occlusal surface of the tooth 48b and an exterior occlusal surface 82 shaped to conform to the occlusal surface of the opposing tooth 48a. The thickness of the occlusal portion between surfaces 80 and 82 is equal to, substantially equal to, or identical to the intra-occlusal space or distance d between the teeth surfaces 66, 68 numbered in FIG. 1A.

Figure 1C:
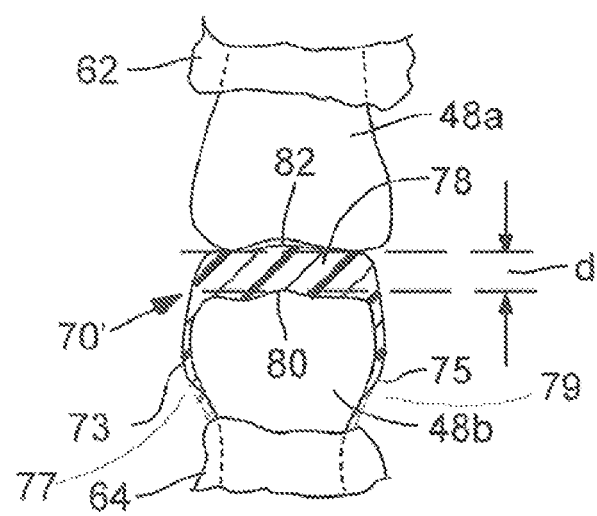
FIG. 1C illustrates the teeth of FIG. 1A with a portion of a dental appliance according to another embodiment shown mounted to the lower tooth and with an occlusal section of the appliance filling the measured intra-occlusal space between the illustrated pair of teeth, as described above for FIG. 1B.

FIG. 1C illustrates a portion 70' of a first posterior or lateral appliance side portion according to another embodiment. The portion 70' includes first and second side walls 73, 75 (side wall 73 being the buccal side wall and side wall 75 being the lingual side wall). The illustrated side walls extend downwardly, i.e., in an apical direction, below the height of contour of the clinical crown 76, and farther, to the gingival line. In some cases, one or both of the side walls can extend slightly below the gingival line. Thus, the side walls 73, 75 engage with the tooth substantially in the undercut regions 77, 79, respectively. The appliance portion 70' comprises an occlusal portion 78 that extends between the side walls 73, 75. As also described above, the occlusal portion has an interior occlusal surface 80 shaped to conform to the occlusal surface of the tooth 48b and an exterior occlusal surface 82 shaped to conform to the occlusal surface of the opposing tooth 48a. The thickness of the occlusal portion between surfaces 80 and 82 is equal to, substantially equal to, or identical to the intra-occlusal space or distance d between the teeth surfaces 66, 68 numbered in FIG. 1A.

Figure 2:
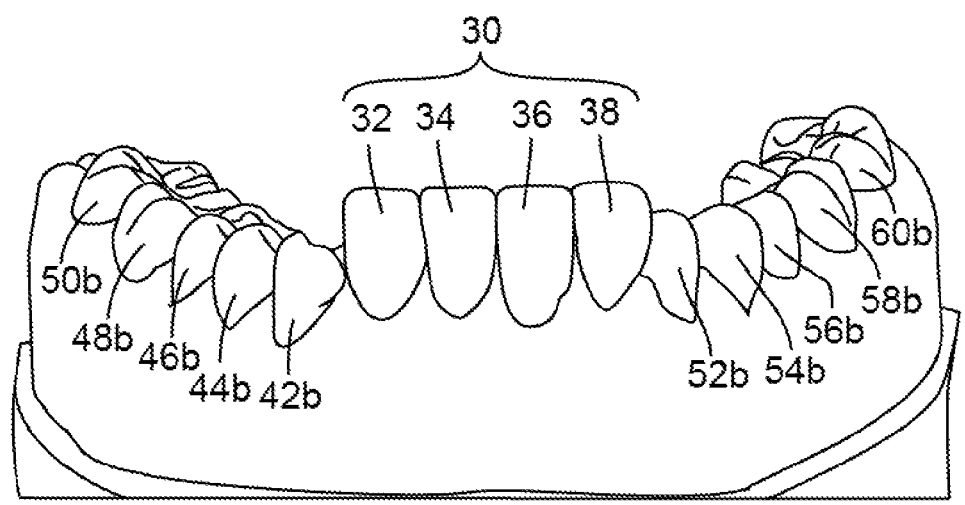
FIG. 2 shows an anterior appliance portion coupled to a model of a user's lower jaw; and more specifically an anterior sectional appliance or front portion-coupled to the front teeth of the user's lower jaw.

FIG. 2 shows a front appliance portion or section 30 coupled to the lower jaw 8; and more specifically coupled to the front teeth, in this example, the incisor teeth, of the lower jaw.

Figure 3:
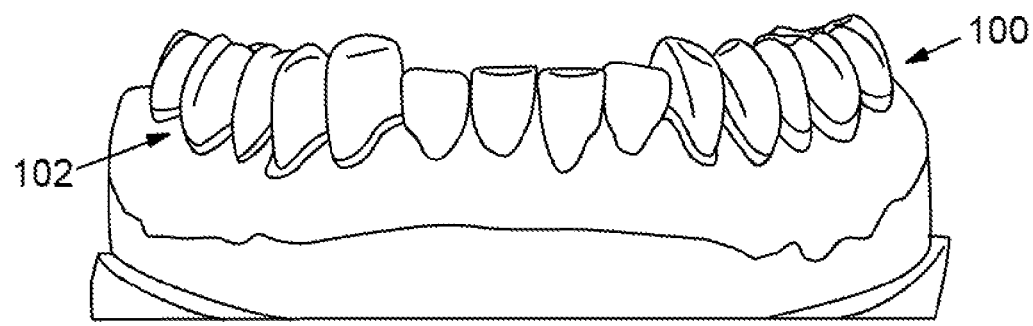
FIG. 3 shows first and second lateral or side portions (e.g., right and left lateral posterior appliance sections) that can be used separately from or in conjunction with the front appliance portion of FIG. 2.

FIG. 3 shows first and second appliance side or lateral portions 100, 102 that can be used separately from or in conjunction with the front appliance portion 30. The appliance portion 30 is not present in this FIG. 3. The appliance portions 100, 102 close the gap or intra-occlusal space that was measured by the provider to be filled in with the appliance. The gap is the intra-occlusal space between the teeth to be covered by first and second lateral portions when the side portions are being worn. In this example, the intra-occlusal space is the distance between the user's respective upper and lower molars, canines and bicuspids when the mandible is in a relaxed position, such as a physiologic rest position, minus the freeway space. To address an asymmetry in the user's facial appearance, the side portions at one side of the user's mouth can be made to extend the height of the teeth to which such side portion is mounted to a greater or to a lesser extent than the height required to close the gap that otherwise would exist when the lower jaw is relaxed. Desirably, the side or lateral appliance portions engage the canines, premolars and molars of the user; but not the incisors of the user, and are independently removable relative to the front appliance portion.

Figure 4:
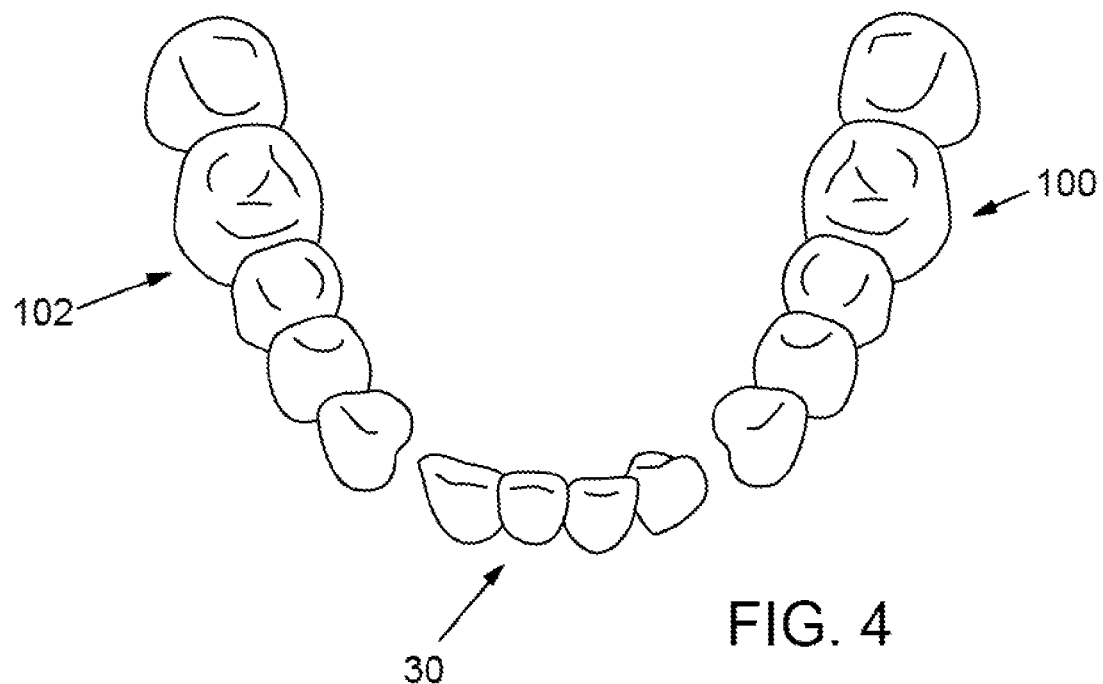
FIG. 4 shows a combination of three piece appliance comprised of three appliance sections that together cover the entire arch of the user; these appliance sections comprise the first and second lateral or posterior appliance sections or portions and an appliance front or anterior appliance section or portion. More specifically.

FIG. 4 shows a three piece appliance comprising appliance side or lateral portions 100, 102 and an appliance front portion 30.

Figure 5:
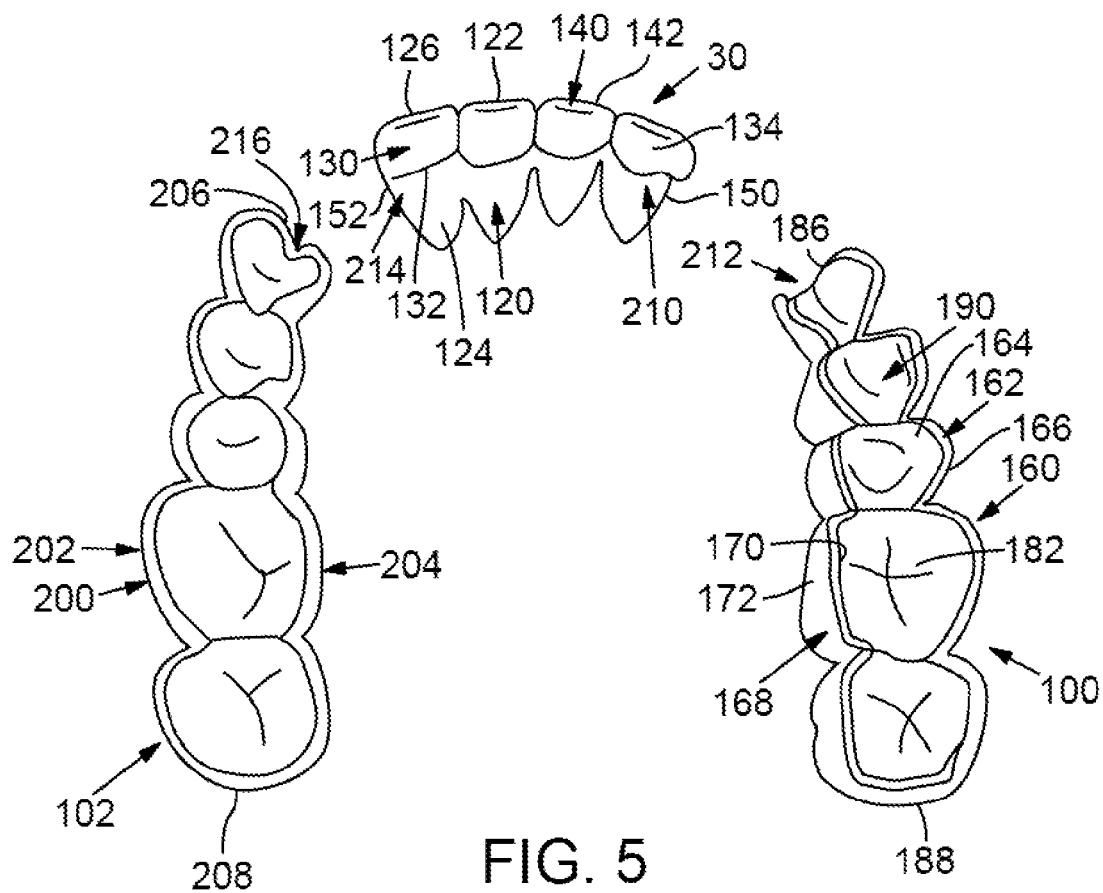
FIG. 5 illustrates a bottom view of the three piece combination appliance of FIG. 4 showing respective teeth receiving pockets between sidewalls of the appliance portions. The pockets each can have a tooth receiving region in the shape of the tooth received by the pocket.
Figure 6:
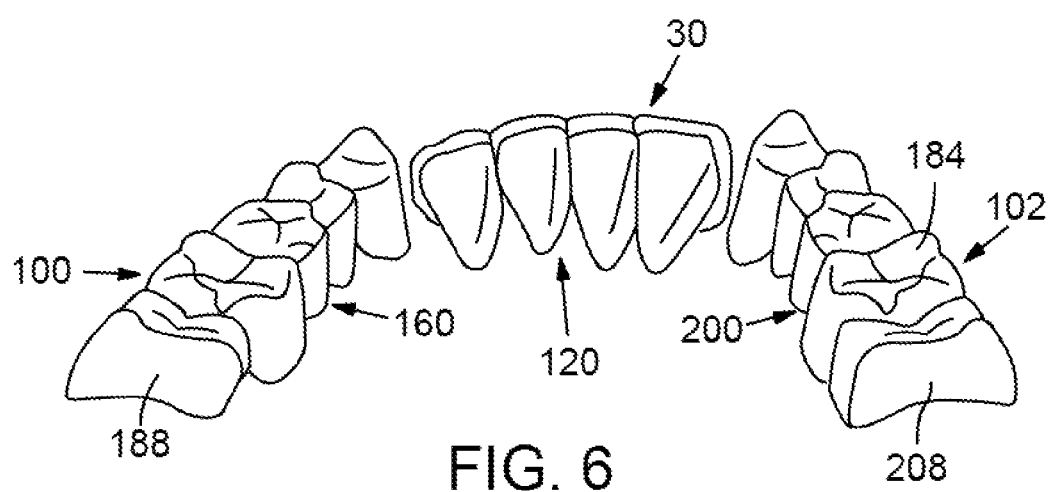
FIG. 6 shows the lingual view of the appliance portions shown in FIG. 4.
Figure 7:
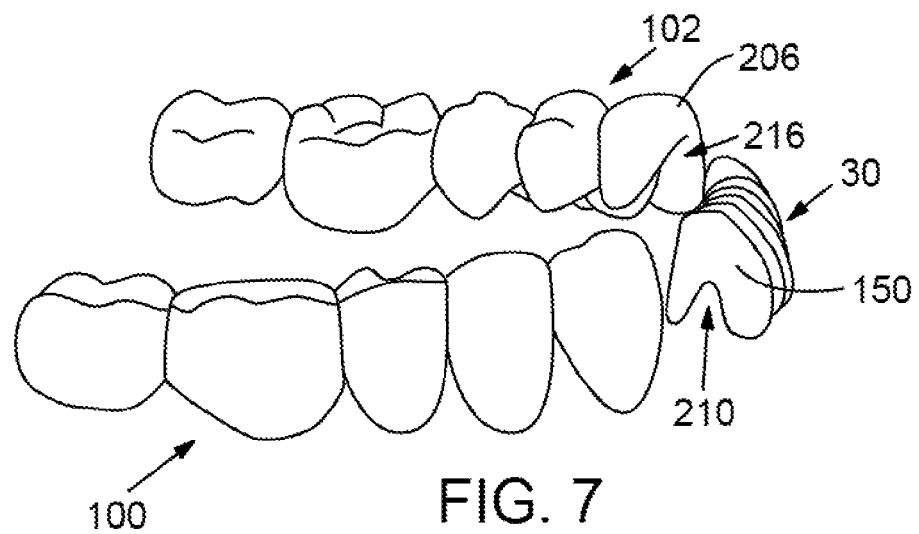
FIG. 7 illustrates a side view of the appliance portions shown in FIG. 4.

FIG. 5 illustrates a bottom or gingival view of the appliance portions of FIG. 4 showing respective teeth receiving pockets between contiguous sidewalls of the appliance portions. FIG. 6 illustrates a top lingual view of the appliance portions of FIG. 4 and FIG. 7 illustrates a side view of these appliance portions.

With reference to FIGS. 3-7, the illustrated front portion 30 is adapted to engage the upper or lower incisors of the user, and in the illustrated example is adapted to engage the lower incisors.

With specific reference to FIG. 5, the front portion 30 comprises a front body portion 120 sized in this example to engage all four lower incisors of the user. The front body portion 120 comprises a contiguous front wall 122 comprising a front wall interior surface 124 adapted to engage the facial or labial surfaces of the engaged upper or lower incisors (in this example the lower incisors) of the user and an opposed front wall exterior surface 126. The illustrated front body portion comprises a contiguous rear wall 130 comprising a rear wall interior surface 132 adapted to engage the lingual surfaces of the engaged upper or lower incisors (in this example of the lower incisors) of the user and a lingual or rear wall exterior surface 134 adapted to face the tongue of the user. The front body portion 120 also comprises a front occlusal wall portion 140 extending between the front wall 122 and the rear wall 130. The front occlusal wall portion 140 comprises a front occlusal wall interior surface adapted to engage the occlusal surfaces of the engaged upper or lower incisors (in this example the lower incisors) of the user. The front occlusal wall portion also comprises a front occlusal wall exterior surface 142 adapted to face the occlusal surfaces of the teeth of the user opposed to the teeth of the user engaged by the front wall portion. In this example occlusal wall surface 142 faces the lower occlusal surfaces of the upper incisors. In addition, the front occlusal wall 140 has a thickness between each pair of opposed teeth that is substantially equal to, equal to or identical to the intra-occlusal space between the respective pairs of opposed upper and lower incisors of the user. The front body portion 130 defines a respective pocket for each of the incisors engaged by the front body portion. The illustrated front body portion 130 also comprises a first front body end portion 150 and a second front body end portion 152. Each pocket desirably has an occlusal surface that conforms to the side and shape of the occlusal surface of the engaged tooth.

With further reference to FIG. 5, each of the posterior or lateral side portions 100, 102 can be identical, except for differences due to the shape of the dentition. Consequently, only the lateral side portion 100 will be described in detail. Side portion 100 comprises a first lateral portion adapted to engage the upper or lower (in this example) the canine, pre-molar and molar teeth, but not the incisor teeth, of a user at the first side 40 of the mouth of the user. In a desirable form, the side portion 102 can engage the canine, pre-molar and molar teeth, but not the incisor teeth, at the second side 41 of the user's mouth. The first lateral portion 100 comprises a first lateral body portion 160 comprising a contiguous first buccal wall 162. The buccal wall 162 comprises first buccal wall interior surface 164 adapted to engage the buccal facial surfaces of the teeth engaged by the first lateral portion and an opposed first buccal wall exterior surface 166. The first lateral body portion 160 also comprises a first lingual wall 168 comprising a first lingual wall interior surface 170 adapted to engage the lingual surfaces of the teeth engaged by the first lateral portion and a first lingual wall exterior surface 172 adapted to face the tongue of the user. The illustrated first lateral body portion also comprises a first occlusal wall portion 180 extending between the first buccal wall 162 and the first lingual wall 168. The first occlusal wall portion comprises a first occlusal wall interior surface 182 adapted to engage and conform to the occlusal surfaces of the teeth of the user engaged by the first lateral body portion. The first occlusal wall portion 180 also comprises a first occlusal wall exterior surface 184 (FIG. 6) facing the occlusal surfaces of the teeth (in this example the upper teeth) of the user opposed to the teeth of the user engaged by the first lateral portion (in this example the lower teeth of the user). The first occlusal wall portion is designed to have a thickness between each pair of opposed upper and lower teeth of the user that is substantially equal to, equal to, or identical to the intra-occlusal space between respective pairs of opposed teeth. In addition, the first lateral body in this example comprises a first lateral body end portion 186 and a second lateral body end portion 188. The illustrated first lateral body portion 160 defines a respective pocket for each of the teeth engaged by the first lateral body portion; one such pocket being indicated at 190 in FIG. 5. The second lateral body portion also defines respective pockets for the received teeth. The pockets are desirably in the shape of, and with surfaces that match the corresponding surfaces, the tooth received in the pocket.

The second lateral side portion also has a second lateral body portion 200 with respective buccal and lingual contiguous walls 202, 204. The second lateral body portion has third and fourth end portions 206, 208. Assuming both the first and second lateral side portions 100, 102 are installed, the first lateral end portion 186 of lateral side portion 160 is positioned adjacent to and desirably abutting the first front body end portion 150 and the third lateral end portion of lateral side portion 200 is positioned adjacent to and desirably abutting the second front body end portion 152. Thus, in this example, the first front body end portion is adapted to be positioned adjacent to the first lateral body end portion and the second front body end portion is adapted to be positioned adjacent to the third lateral body end portion when the front body portion, and first and second lateral portions are worn by a user.

Desirably, the first front body end portion 186 and the front body portion 130 is movable upwardly and downwardly relative the first lateral body end portion 186 and relative to the first lateral body portion 160. In addition, desirably the second front body end portion is movable upwardly and downwardly relative to the third lateral body end portion 206 when the front portion and lateral side portions of the appliance are worn by a user.

As explained above, the front body portion can comprise an occlusal portion having a thickness that is substantially equal to, equal to, or identical to the intra-occlusal spaces or between the upper and lower incisors of the user; the first lateral body portion can comprise a first lateral body occlusal portion having a thickness that is substantially equal to, equal to, or identical to the intra-occlusal spaces between the upper and lower canine teeth, pre-molars and molars at the first side of the user's mouth; and the second lateral body portion can comprise a second lateral body occlusal portion having a thickness that is substantially equal to, equal to, or identical to the intra-occlusal spaces between the upper and lower canine teeth, pre-molars and molars at the second side of the user's mouth.

In the embodiment of FIGS. 4-6, the front appliance portion and first and second lateral appliance portions are separate and independent disconnected components. That is, the first front body end portion 150 is disconnected from and separate from the first lateral body end portion 186 and the second front body end portion 152 is disconnected from and separate from the third lateral body end portion 206. In addition, a respective void can be provided in each of the front body end portions 150, 152 and in the first and third lateral body end portions 186, 206, which facilitates positioning the adjacent end portions of the front and first and second lateral end portions next to one another and desirably abutting one another. An exemplary void at the first front end portion 150 is indicated at 210 in FIG. 7; an exemplary void at first lateral end portion 186 is indicated at is indicated at 212 in FIG. 5; an exemplary void at the second front end portion 152 is indicated at 214 in FIG. 5, and an exemplary void at the third lateral end portion 206 is indicated at 216 in FIG. 7.

In the embodiment illustrated in FIGS. 5 and 6, the wall of the second body end portion 188 of the first lateral body portion 160 can be and is shown adapted to surround the rear most engaged molar of the user at the first side of the user's mouth when the first lateral portion 100 is worn by the user. In addition, the wall of the fourth body end portion 208 of the second lateral body portion 200 can be and is shown adapted to surround the rear most engaged molar of the user at the second side of the user's mouth when the second lateral portion 102 is worn by the user.

In the embodiment illustrated in FIGS. 5-7, the front appliance portion 30 and first and second lateral appliance portions 100, 102 are shown as each being adapted for mounting to and engagement by respective lower teeth of the user.

The front and rear walls of the front body portion can be of a uniform thickness, and the first and second buccal walls and first and second lingual walls of the first and second lateral portions can be of a uniform thickness. The thickness of the buccal and lingual walls of the lateral appliance portions, and also of the front portion can be thin, such as equal to, substantially equal to, or identical to from 0.3 to 0.6 mm thick. For a comfortable fit, a clearance or cement space of typically from 30-100 microns between the teeth surfaces and corresponding appliance surfaces, such as for temporary adhesive.

Figure 8:
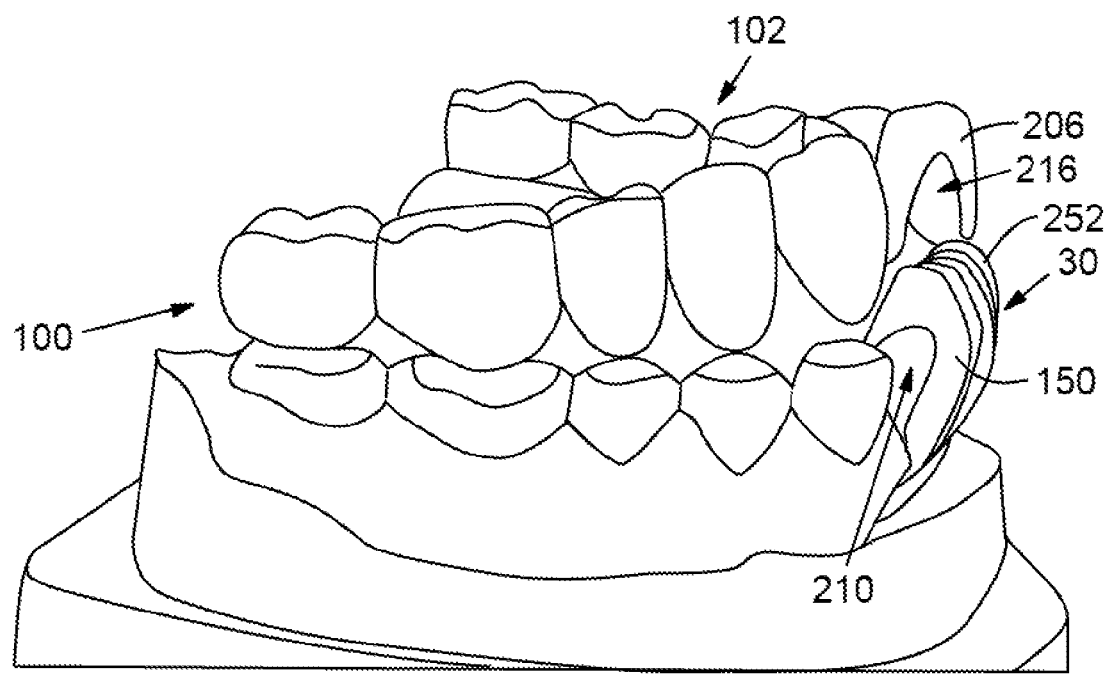
FIG. 8 illustrates the installation of the posterior appliances or first and second side portions-of the appliance, the front or anterior appliance or appliance portion having already been installed in FIG. 8.

FIG. 8 illustrates the installation of first and second lateral appliance portions 100, 102 with the front appliance portion 30 shown installed.

Figure 9:
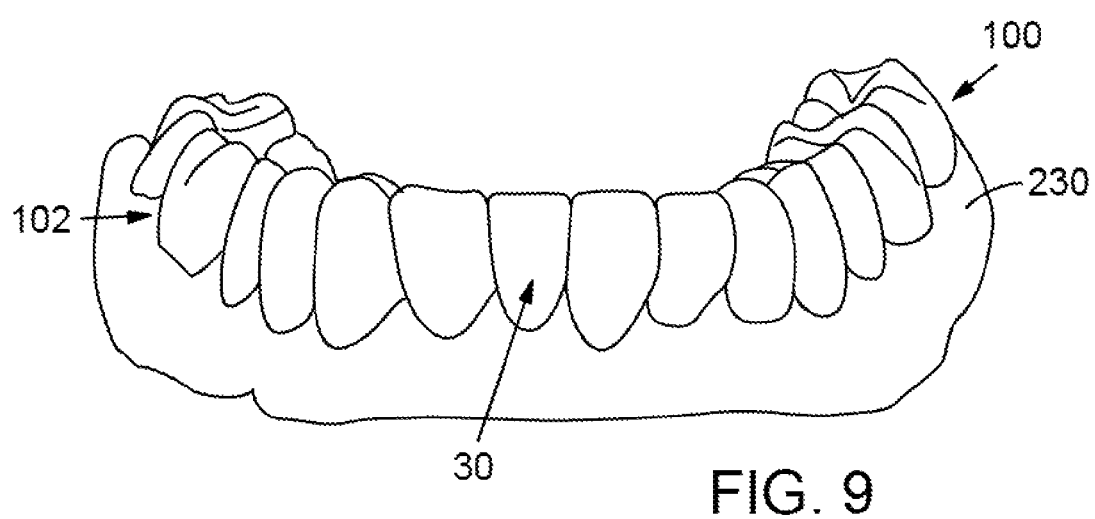
FIG. 9 illustrates a front or anterior view of the combination of appliance sections of FIG. 4 when fully installed.
Figure 10:
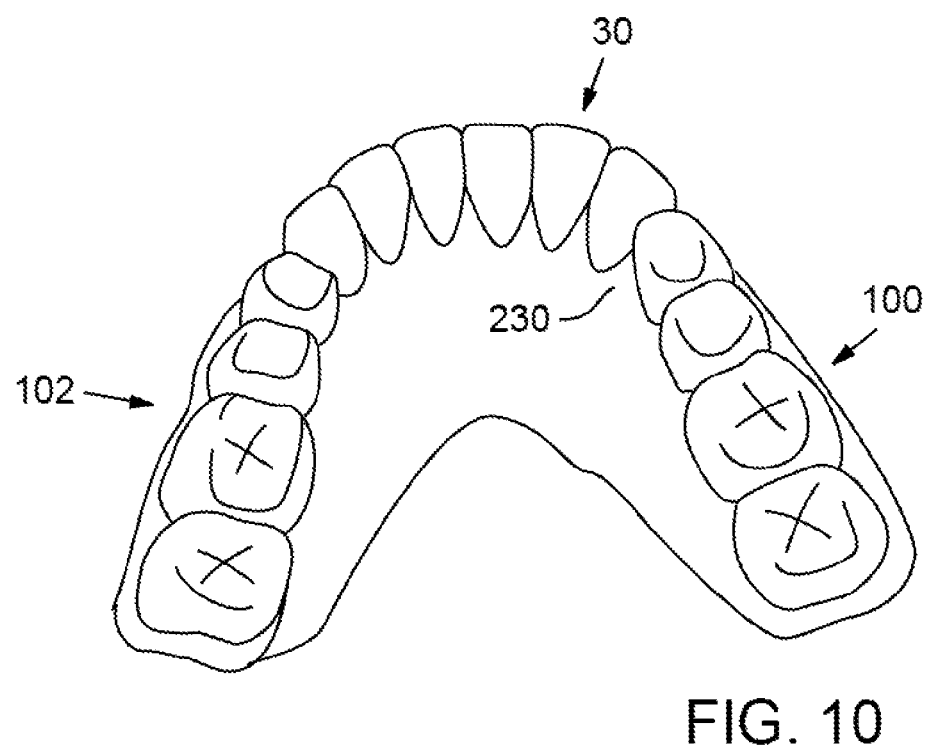
FIG. 10 is a top or occlusal view of the installed appliance of FIG. 4 looking from the rear or posterior toward the front of the lower jaw to which the appliance sections are mounted.

FIGS. 9 and 10 illustrate the user's lower teeth and a portion of the user's gums with the appliance portions 30, 100 and 102 being worn by the user.

In an alternative embodiment, a first link can be provided to interconnect the first front body end portion and the first lateral body end portion and a second pivot link can be provided that that interconnects the second front body end portion and the third lateral body end portion; the first and second links desirably allowing relative upward and downward movement of the interconnected body end portions, but restrict lateral movement of the end portions.

Figure 11:
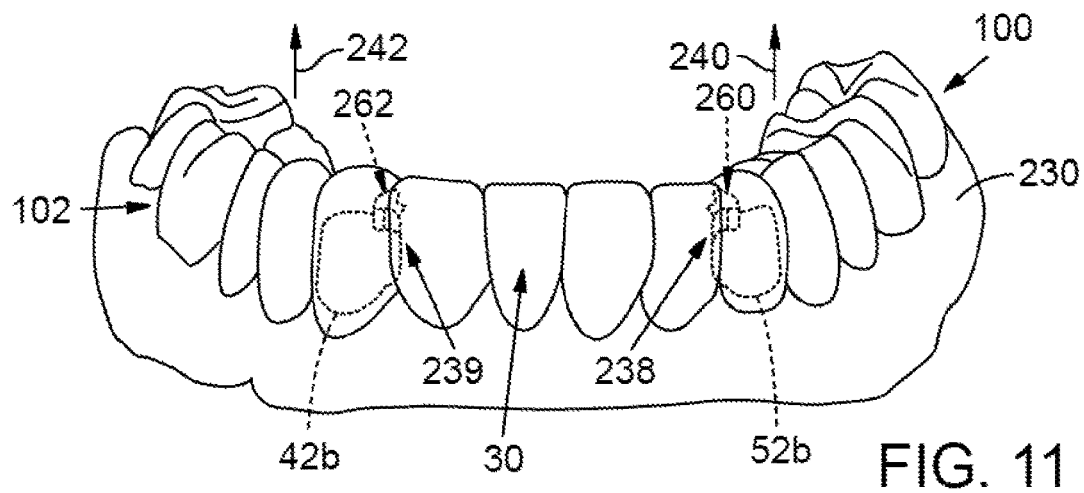
FIG. 11 is a front view of exemplary front and posterior appliance portions with an embodiment of a first interlocking joint structure shown that detachably interconnects the mesial end of the left lateral posterior appliance portion with the left distal end of the front or anterior appliance portion and an embodiment of a second interlocking joint structure, which in this embodiment is like the first interlocking joint structure, that detachably interconnects the mesial end of the right lateral posterior appliance portion with the right distal end of the front or anterior appliance.
Figure 12:
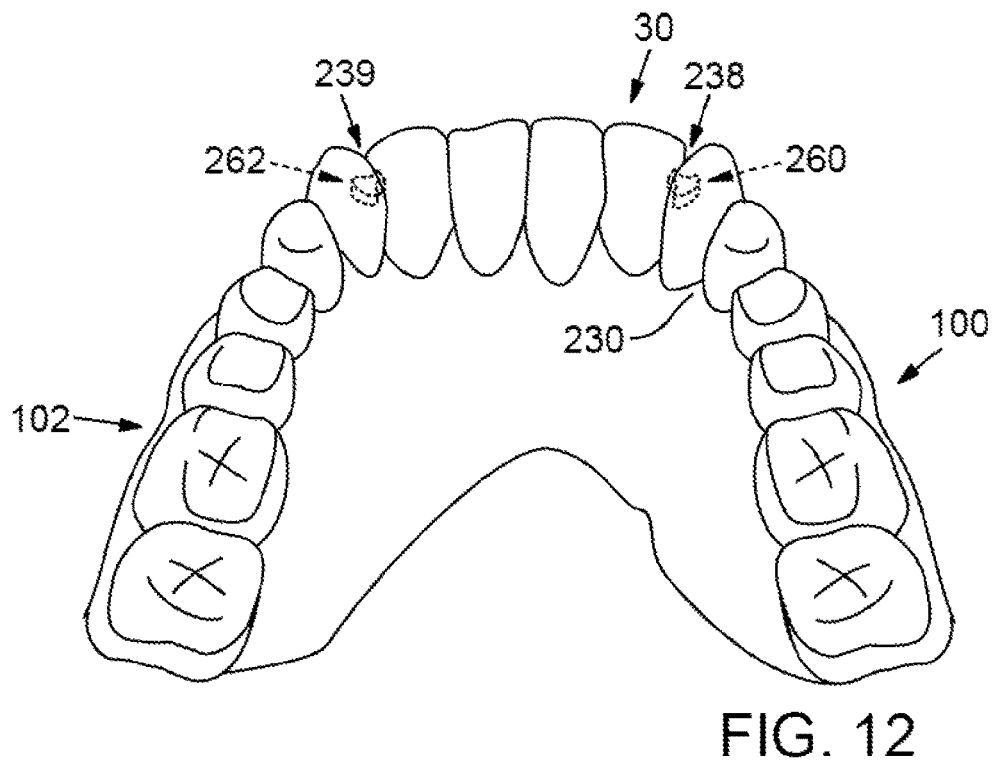
FIG. 12 is a top or occlusal anterior view of a plural piece appliance with interlocking joint structures of FIG. 11.
Figure 13:
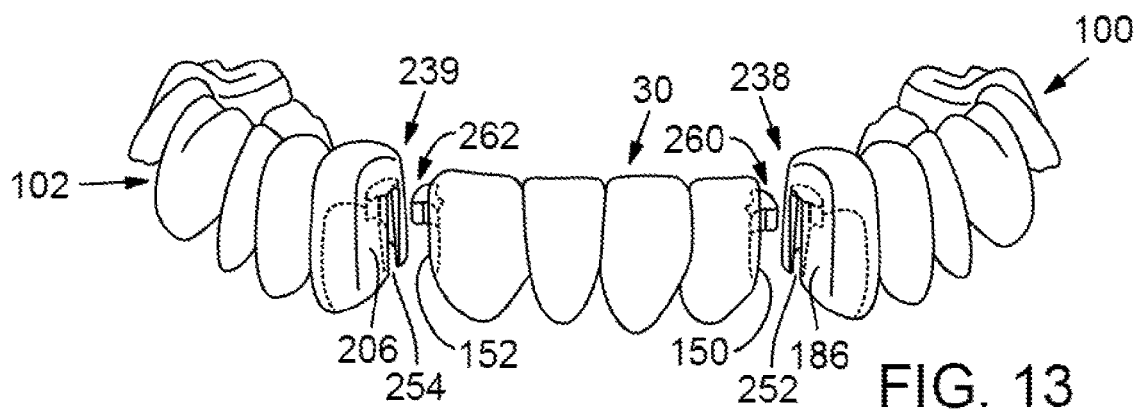
FIG. 13 illustrates the anterior and bilateral posterior appliances or appliance portions-with the interlocking joints disconnected and shows the independence of the appliances or appliance portions from one another.

Thus, with reference to FIGS. 11-13, the end portions of the independent appliance portions can be detachably interconnected when worn. Thus, anterior section or appliance portions can be detachably linked to adjacent end portions of the lateral sections in a manner that permits relative upward and downward movement of the linked end portions, but that restricts relative lateral movement of the linked end portions and the user's anterior and posterior teeth. A non-load bearing structure such as a pivot or band that permits this relative movement can be used, such as a rest seat or polymer band connector.

As a specific example, at the anterior end portions of each of the posterior appliance portions 100, 102 and the respective adjacent end portions 150, 152 of the anterior appliance portion 30 (see FIG. 13) an interlocking joint can be provided. An example of these joints is indicated at 238, 239 in FIGS. 11-13. The illustrated joints 238, 239 permit upward and downward movement of at least one of the adjacent appliance end portions. For example, the upwardly facing arrows 240, 242 in FIG. 11 indicate a direction of motion of posterior sections 100, 102 and their respective anterior end portions 186, 206 relative to the end portions 150, 152 of the front appliance portion 30. The illustrated joints restrict or prevents lateral relative movement of such end portions 150, 186 and 152, 206 and the teeth overlaid by such end portions (e.g., the adjacent canine teeth and incisors).

In one form, the interlocking joint comprises a projection at the end of one of the adjacent posterior and anterior appliance portions and an upright receiving slot at the end of the other of the adjacent posterior and anterior appliance ends. In FIG. 13, a slot 252 is provided in the anterior end of posterior end portion 186 and a slot 254 is provided in the end of posterior end portion 206. In addition, a projection 260 is provided in the end of end portion 150 of the anterior appliance portion 30 and a projection 262 is provided in the end of end portion 152 of anterior appliance portion 30. The positioning of the adjacent projections and slots can be reversed with the slot being positioned at the adjacent end of appliance portion 30 and the projection at the adjacent end of the posterior appliance portion, if desired. By positioning the projections 260, 262 within the respective adjacent slots 252, 254, the relative lateral motion of the adjacent ends of the appliance portions is restricted or prevented. As a result, relative lateral movement of the anterior and posterior teeth covered by such ends of the anterior and posterior appliance portions is restricted or prevented. However, the projections 260, 262 can desirably slide upwardly and downwardly relative to their respective receiving slots 252, 254 to relieve stress on the appliance portions at their abutting end locations during, for example, chewing by the user.

In addition, desirably each appliance portion with the slot remains a separate element from the appliance portion with the projection so that the slotted appliance portion can be lifted upwardly and removed from the user's mouth separately from the adjacent appliance portion with the projection. For example, in FIG. 11, the posterior appliance portions 100, 102 with the respective slots 252, 254 can be moved upwardly independently as indicated by respective arrows 240, 242 and away from the user's teeth and appliance portion 30. If there are two posterior portions and one anterior portion with adjacent ends, this interlocking structure can be provided at each set of adjacent end portions as shown in FIGS. 11-13.

In a specific example, as shown in FIGS. 11-13, the interlocking structures or joints 238, 239 can comprise a dove tail joint with a tenon portion comprising the projection and a mortise portion comprising the slot. The tenon can be flared to engage end walls defining the slot to hold the interlocking joint together while still permitting upward movement of one or both of the appliance portions relative to one another.

In addition, the slots 252, 254 can be oriented to be parallel to the draw or angular inclination (e.g, the posterior teeth are angled lingually and the slots can be oriented to be parallel to the angle of inclination of the canine tooth at the end of the posterior appliance portions adjacent to the end of the adjacent anterior appliance portion). The slots can be open at the top to permit either anterior or posterior appliance portions to be moved upwardly (with the projection sliding relative to the slot) and independently removed from the user's mouth. The occlusal surface of the projection or projections can be positioned and shaped to match the occlusal surface of the opposed tooth. Alternatively, the slot can be closed at the top; in which case the appliance portion with the slot can be moved upwardly to clear the slot and the user's mouth prior to removing the appliance portion with the projection.

In an alternative approach, where the user's face has aesthetically undesirable asymmetry, (e.g., sags on one side of the user's face relative to the other side of the user's face), more material can be added to the appliance section at the sagging side, such as up to the amount required to place the user's face in the fully relaxed state, with less material being added to the section of the appliance at the other or opposite side of the user's face to reduce the asymmetry of the user's face when the appliance sections are worn.

At the discretion of the provider and as needed by the patient or user, the intended use of the appliance will be determined by the prescribing doctor.

The disclosed appliance components or sections can be worn during the day or night as a removable appliance for chewing and function. The components can also be adhered to the teeth temporarily, such as with any FDA approved temporary dental cements, for the purpose of stability and safety during chewing or nighttime wear.

The appliance, when worn, can also be used by the treating provider to address temporomandibular joint (TMJ) conditions and bruxism because of the resulting muscle relaxation and bite stabilization. The appliance may also eliminate the need for non-reversible procedures such TMJ surgical procedures. TMJ noise such as popping, clicking or grinding noise in the jaw joints, pain during chewing, limited mouth opening and limited range of motion when deviating the lower jaw to the right or left, are among the most common symptoms when a patient suffers from tension headaches, TMJ disorders, or a poor facial profile. The majority of TMJ damage and associated muscle pain stems from a pathologic occlusion. Currently the majority of removable TMJ orthotics and night guards are made of bulky acrylic appliances which are non-functional; meaning that the patient cannot chew or function with them. The main problem with the existing full arch one piece appliances are that, when the patient takes out the appliance to eat, their jaw may drift into the habitual bite position which may cause the patient to regress back to the muscle spasm and symptomatic jaw position. By providing the patient with a removable, yet anatomical and tooth colored appliance which supports their mandibular rest position even during chewing and function, and since dental occlusion is a determinant of the mandibular posture, a functional appliance as disclosed herein that may speed up the healing process of the TMJ joints and muscle. The appliance sections overlay the existing natural dentition, change the occlusion temporarily, and hold the jaw in a different position that is more desirable to the patient. Because of the anatomical configuration (teeth shaped configuration of the occlusal surfaces) of the appliance sections, a user can chew and function comfortably while wearing the device.

Throughout this disclosure, when a reference is made to a first element being coupled to a second element, the term "coupled" is to be construed to mean both direct connection of the elements as well as indirect connection of the elements by way of one or more additional intervening elements. Also, the singular terms "a", "and", and "first", mean both the singular and the plural unless the term is qualified to expressly indicate that it only refers to a singular element, such as by using the phase "only one". Thus, for example, if two of a particular element are present, there is also "a" or "an" of such element that is present. In addition, the term "and/or" when used in this document is to be construed to include the conjunctive "and", the disjunctive "or", and both "and" and "or". Also, the terms "includes" and "has" have the same meaning as "comprises" and the terms "including" and "having" have the same meaning as "comprising". The term "substantially equal" to a dimension or range means within plus or minus ten percent of the dimension or range; the term "equal" to the dimension or range means within plus or minus five percent of the dimension; and the term "identical" to a dimension or range means the exact dimension within manufacturing tolerances. Thus, the phrase substantially equal to a freeway space that ranges from 2 to 3 mm is within plus or minus ten percent of this range of freeway space. The term tooth or teeth refers to natural teeth, and also includes other forms of dentition such as dental bridges, arches and tooth implants. Thus, for example, the reference to a canine tooth encompasses a natural canine tooth of an individual, as well as any artificial replacement for the canine tooth.

Having illustrated and disclosed the principles of our developments by a number of exemplary embodiments, it should be apparent that these embodiments can be changed in arrangement and detail without departing from the inventive principles disclosed herein. All such variations are within the scope of this disclosure. We therefore claim as our invention all that comes within the scope and these claims.

The invention claimed is:

1. A dental appliance for occupying the intra-occlusal space between opposed upper and lower pairs of teeth of a user of the dental appliance, the intra-occlusal space being the space or distance between the opposed upper and lower teeth measured when the user's mandible is in a relaxed position, minus a freeway space, the dental appliance comprising:

first and second dental appliance components, wherein the first dental appliance component is for a first side of the user's mouth and the second dental appliance component is for the second side of the user's mouth, wherein each of the first and second dental appliance components comprises a lateral body that defines teeth receiving pockets that are adapted to receive and engage one of upper and lower posterior teeth of the user at a respective side of the user's mouth to retain the lateral body in place, the lateral body comprising a lateral body occlusal portion having a thickness selectively dimensioned to substantially equal to the intra-occlusal space between the upper and lower posterior teeth at the respective side of the user's mouth and a lateral body exterior occlusal surface that is shaped to contact and conform to opposing natural teeth;

first and second lateral body end portions, wherein a first of the teeth receiving pockets at the first lateral body end portion is shaped to resiliently engage a first posterior tooth at the respective side of the user's mouth and a second of the teeth receiving pockets at the second lateral body end portion is shaped to resiliently engage a second posterior tooth at the respective side of the user's mouth, thereby retaining the lateral body in place by snap-fit mechanical retention;

a lateral body apical portion extending apically from the lateral body occlusal portion, the lateral body apical portion extending apically at least past a height of a contour of a respective crown thereof for each of the engaged teeth, the apical portion having a buccal wall with a buccal wall interior surface that is configured to resiliently engage buccal facial surfaces of the engaged teeth and an opposed buccal wall exterior surface shaped to mimic natural teeth anatomy, and a lingual wall with a lingual wall interior surface that is configured to resiliently engage lingual surfaces of the engaged teeth and an opposed lingual wall exterior surface shaped to mimic natural teeth anatomy, wherein the lingual wall has a lingual wall thickness of 0.3 mm to 0.6 mm to preserve tongue space within the user's dental arch, and a third appliance component separately removable relative to the first and second appliance components, the third appliance component having a functional front body that defines teeth receiving pockets adapted to resiliently engage one or more of the upper or lower anterior teeth of the user to retain the third appliance component in place, the front body comprising a front body occlusal portion having a thickness that is substantially equal to the intra-occlusal space between the upper and lower anterior teeth of the user and a front body exterior occlusal surface shaped to contact and conform to opposing natural teeth;

wherein the first and second dental appliance components are functional when worn by the user, permitting movement and occlusal contacts between the lateral body exterior occlusal surface of the first dental appliance component and the opposing natural teeth on the first side of the user's mouth and between the lateral body exterior occlusal surface of the second dental appliance component and the opposing natural teeth on the second side of the user's mouth, to enable functional occlusion allowing speech, mastication and swallowing.

2. The dental appliance of claim 1, wherein the lateral body apical portion extends apically to a gingival line for each of the engaged teeth.

3. The dental appliance of claim 1, wherein the lateral body apical portion is shaped to contact and conform to a gingival line for each of the engaged teeth.

4. The dental appliance of claim 1, wherein ends of the apical portion are scalloped shaped to follow a gingival line for each of the engaged teeth.

5. The dental appliance of claim 1, wherein each lateral body comprises a middle portion positioned between the first and second end portions, and wherein the middle portion comprises at least a third pocket shaped to resiliently engage a third posterior tooth.

6. The dental appliance of claim 1, wherein each lateral body comprises a middle portion positioned between the first and second end portions, wherein the middle portion is shaped to fill a space of at least one missing natural tooth between the first posterior tooth and the second posterior tooth.

7. The dental appliance of claim 1, wherein the lingual wall thickness is 0.4 mm to 0.6 mm.

8. The dental appliance of claim 1, wherein the buccal wall has a buccal wall thickness of 0.3 mm to 0.6 mm.

9. The dental appliance of claim 1, wherein the buccal wall thickness is 0.4 mm to 0.6 mm.

10. The dental appliance of claim 1, wherein at least one of the lingual wall and the buccal wall has a varying thickness.

11. The dental appliance of claim 1, wherein the third appliance component extends apically to a gingival line for each of the engaged teeth of the third appliance component.

12. The dental appliance 1, wherein at least two of the first appliance component, the second appliance component and the third appliance component are formed to have respective lines of draw that are different from each other based on differing inclinations of the respective engaged teeth.

13. The dental appliance of claim 1, wherein each lateral body exterior occlusal surface and each buccal wall are joined to each other at a smoothly curving transition to mimic natural tooth anatomy.

14. The dental appliance of claim 1, wherein each lateral body exterior occlusal surface and each lingual wall are joined to each other at a smoothly curving transition to preserve tongue space.

15. The dental appliance of claim 1, wherein the teeth receiving pockets are sized to provide the snap-fit mechanical retention without requiring alteration of shapes of the engaged teeth.

16. The dental appliance of claim 1, wherein each lateral body apical portion extends apically by a distance sufficient to engage an undercut portion of the engaged teeth.

17. A dental appliance for occupying the intra-occlusal space between opposed upper and lower pairs of teeth of a user of the dental appliance, the intra-occlusal space being the space or distance between the opposed upper and lower teeth measured when the user's mandible is in a relaxed position, minus a freeway space, the dental appliance comprising:
- a first dental appliance component comprising a lateral body that defines teeth receiving pockets that are adapted to receive and engage one of upper and lower posterior teeth of the user at a first side of the user's mouth to retain the lateral body in place, the lateral body comprising a lateral body occlusal portion having a thickness selectively dimensioned to substantially equal to the intra-occlusal space between the upper and lower posterior teeth at the first side of the user's mouth and a lateral body exterior occlusal surface that is shaped to contact and conform to opposing natural teeth;
- first and second lateral body end portions, wherein a first of the teeth receiving pockets at the first lateral body end portion is shaped to resiliently engage a first posterior tooth at the first side of the user's mouth and a second of the teeth receiving pockets at the second lateral body end portion is shaped to resiliently engage a second posterior tooth at the first side of the user's mouth;
- a lateral body apical portion extending apically from the lateral body occlusal portion, the lateral body apical portion extending apically approximately to a height of a contour of a respective crown thereof for each of the engaged teeth, the lateral body apical portion having
  - a buccal wall with a buccal wall interior surface that is configured to resiliently engage buccal facial surfaces of the engaged teeth and an opposed buccal wall exterior surface shaped to mimic natural teeth anatomy, and
  - a lingual wall with a lingual wall interior surface that is configured to resiliently engage lingual surfaces of the engaged teeth and an opposed lingual wall exterior surface shaped to mimic natural teeth anatomy,
  - wherein the lingual wall has a lingual wall thickness of 0.3 mm to 0.6 mm to preserve tongue space within the user's dental arch,
  - wherein the lateral body apical portion does not contact any undercut portions of engaged teeth; and
- a second dental appliance component separately removable relative to the first appliance component, the second appliance component having a front body that defines teeth receiving pockets adapted to resiliently engage one or more of the upper or lower anterior teeth of the user to retain the second appliance component in place, the front body comprising a front body occlusal portion having a thickness that is substantially equal to the intra-occlusal space between the upper and lower anterior teeth of the user and a front body exterior occlusal surface shaped to contact and conform to opposing natural teeth, wherein the second appliance component has a second line of draw different than a first line of draw for the first appliance component,
- wherein the first and second dental appliance components are functional when worn by the user, permitting movement and occlusal contacts between the lateral body exterior occlusal surface and the opposing natural teeth, and between the front body exterior occlusal surface and the opposing teeth, respectively, to enable functional occlusion allowing speech, mastication and swallowing.

18. The dental appliance of claim 17, wherein at least the first and second teeth receiving pockets are configured to receive natural teeth to which bonding material is applied to enhance retention of the dental appliance.

19. The dental appliance of claim 1, wherein at least the first and second teeth receiving pockets are configured to receive natural teeth to which bonding material is applied to enhance retention of the dental appliance.

* * * * *